United States Patent
Lok et al.

(10) Patent No.: US 6,534,436 B2
(45) Date of Patent: Mar. 18, 2003

(54) METHOD FOR THE PRODUCTION OF COBALT CATALYSTS SUPPORTED ON SILICON DIOXIDE AND THEIR USE

(75) Inventors: Cornelis M Lok, Cleveland (GB); Stephen Bailey, Richmond (GB); Gavin Gray, Cleveland (GB)

(73) Assignee: Imperial Chemical Industries PLC, London (GB)

( * ) Notice: Subject to any disclaimer, the term of this patent is extended or adjusted under 35 U.S.C. 154(b) by 0 days.

(21) Appl. No.: 10/202,900

(22) Filed: Jul. 26, 2002

(65) Prior Publication Data

US 2003/0032684 A1 Feb. 13, 2003

Related U.S. Application Data

(63) Continuation of application No. PCT/GB01/00702, filed on Feb. 20, 2001.

(30) Foreign Application Priority Data

Feb. 21, 2000 (GB) ............................................. 0003961

(51) Int. Cl.⁷ .......................... B01J 21/08; C07C 27/00; C07C 45/00; C07C 5/00; C07C 5/03
(52) U.S. Cl. ....................... 502/260; 502/162; 502/167; 518/715; 568/389; 568/398.8; 568/399; 568/881; 568/885; 568/950; 585/250; 585/260; 585/270; 585/274; 585/277
(58) Field of Search ............................... 502/260, 162, 502/167; 518/715; 568/950, 389, 398.8, 399, 881, 885; 585/250, 260, 270, 274, 277

(56) References Cited

U.S. PATENT DOCUMENTS

| | | | | |
|---|---|---|---|---|
| 4,052,335 A | * | 10/1977 | Michalczyk et al. | 252/446 |
| 4,093,450 A | * | 6/1978 | Doyle et al. | 75/35 AA |
| 4,439,544 A | * | 3/1984 | Carter et al. | 502/234 |
| 4,837,193 A | * | 6/1989 | Akizuki et al. | 502/242 |
| 5,036,032 A | * | 7/1991 | Iglesia et al. | 502/260 |
| 5,409,877 A | * | 4/1995 | Takeuchi et al. | 502/245 |
| 5,874,381 A | * | 2/1999 | Bonne et al. | 502/327 |
| 6,075,062 A | * | 6/2000 | Zennaro et al. | 518/715 |
| 6,090,742 A | * | 7/2000 | Culross | 502/258 |
| 6,376,622 B1 | * | 4/2002 | Hucul | 525/338 |

FOREIGN PATENT DOCUMENTS

| | | |
|---|---|---|
| EP | 0168096 | 1/1986 |
| GB | 629534 | 7/1946 |
| WO | WO 96/04072 | 2/1996 |

OTHER PUBLICATIONS

Nitta et al., "Selective Hydrogenation of α, β–Unsaturated Aldehydes on Cobalt–Silica Catalysts Obtained from Cobalt Chrysotile" *Applied Catalysis* 56 (1989) 9–22. May 1989.
Vainshtein et al., "Influence of the Particle Size of the Heterogeneous Catalyst on the Kinetics of Liquid–Phase Oxidation of Tetralin" *J. Appl Chem USSR* 59 (May 1986) 1057–1058. (Abstract).

\* cited by examiner

*Primary Examiner*—Mark L. Bell
*Assistant Examiner*—Patricia L. Hailey
(74) *Attorney, Agent, or Firm*—Pillsbury Winthrop LLP

(57) ABSTRACT

The invention relates to catalysts comprising cobalt supported on a solid silica support and, in particular, to a method for manufacturing such catalysts. The catalysts may be prepared by slurrying a silica powder or impregnating a silica particle with a solution of a cobalt compound, cobalt amine carbonate, and aging the resulting slurry or solid at elevated temperature; the cobalt amine carbonate is decomposed and precipitated as basic cobalt carbonate onto the silica support. Preferably, the catalysts have a cobalt surface area in the range of 25 to >100 m2 per gram total cobalt. The catalyst may be used in hydrogenation reactions, Fischer-Tropsch reactions and oxidation reactions.

14 Claims, No Drawings

METHOD FOR THE PRODUCTION OF COBALT CATALYSTS SUPPORTED ON SILICON DIOXIDE AND THEIR USE

CROSS REFERENCE TO RELATED APPLICATION

This application is a continuation application based on International Application No. PCT/GB01/00702, filed Feb. 20, 2001, which further claims priority from British Application No. 0003961.0, filed Feb. 21, 2000.

This invention relates to catalysts comprising cobalt supported on a solid silica support and in particular to a method for manufacturing such catalysts.

Catalysts comprising cobalt on a support such as silica or alumina are known in the art for hydrogenation reactions, e.g. for the hydrogenation of chemicals such as aldehydes and nitrites, fats and oils and for the preparation of hydrocarbons from synthesis gas via the Fischer-Tropsch reaction.

WO-A-96/04072 discloses a cobalt on transition alumina catalyst containing between 3 and 40% by weight of cobalt and having a cobalt surface area greater than 30 $m^2/g$ cobalt.

EP-A-0013275 discloses coprecipitated cobalt-silica hydrogenation catalysts prepared by adding an alkaline precipitating agent to a heated mixture containing cobalt cations, silicate anions and solid porous carrier particles under agitation thereby to precipitate the cobalt and silicate ions onto the solid support particles.

EP-A-0029675 discloses coprecipitated nickel hydrogenation catalysts prepared by adding an alkaline precipitating agent to a heated mixture containing cobalt cations, aluminium anions and solid porous particles under to precipitate the nickel and aluminium ions onto the solid support particles.

In certain reactions it may be beneficial to use cobalt deposited on a silica support rather than cobalt on alumina because the acid sites present on alumina may promote undesirable reactions, e.g. it may reduce the selectivity to primary amines in the hydrogenation of nitrites. Furthermore silica supported catalyst may be preferred for use in acid reaction media where gamma alumina supports may show a tendency to dissolve to some extent.

In comparison with other catalytic metals such as copper and nickel used for hydrogenation reactions, cobalt is a relatively expensive and so, to obtain the optimum activity, it is desirable that as much as possible of the cobalt present is in an active form accessible to the reactants. It is therefore desirable to maximise the surface area of the cobalt in the supported catalysts.

Accordingly we now provide a process for manufacturing a catalyst which comprises a cobalt species on a solid silica support, comprising mixing together particles of a solid silica support and an aqueous solution of cobalt ammine carbonate, and heating to an elevated temperature sufficient to effect decomposition of the cobalt ammine carbonate and precipitation of a basic cobalt carbonate onto said support.

In one embodiment of the invention we provide a method of making a catalyst comprising a cobalt species on a silica support, comprising the steps of mixing a silica particulate material with an aqueous solution of a soluble cobalt compound, heating the mixture of p articulate material and cobalt compound to effect precipitation of a basic cobalt carbonate species on the silica, filtering the solid residue from the aqueous medium, and drying.

In a further embodiment of the invention we also provide a process for the production of a catalyst comprising saturating silica support particles with an aqueous solution of cobalt ammine carbonate, and removing the excess of the solution, before heating the resulting product to a temperature sufficient to effect decomposition of the cobalt ammine carbonate.

The solid residue comprising the catalyst may be calcined and, optionally, reduced.

The term "cobalt species" is used broadly to include both elemental cobalt and cobalt in combined form, e.g. as compounds such as cobalt oxides and cobalt hydroxycarbonates. The catalyst in its reduced form is useful for catalysing hydrogenation reactions. The catalyst may, however, be provided as a precursor wherein the cobalt is present as one or more compounds, such as oxides or hydroxy carbonates, reducible to elemental cobalt. In this form, the material may be a catalyst precursor and may be treated to reduce the cobalt compounds to metallic cobalt or the material may itself be a catalyst and used as supplied, e.g. for oxidation reactions. The cobalt surface area figures used herein apply to the material after reduction, but the invention is not limited to the provision of reduced catalyst.

By the term total cobalt, we mean the amount of cobalt whether present in elemental or combined form. Generally however at least 70% by weight of the total cobalt in the reduced catalyst will be in the elemental state.

The catalysts of the invention preferably have a cobalt to silicon atomic ratios in the range 0.01 to 50, particularly 0.03 to 25 and especially 0.05 to 10.

The particulate silica may be formed from natural sources, e.g. as kieselguhr, or may be a synthetic, e.g. precipitated silica. The particulate silica may be in the form of a powder or a shaped granular material, e.g. as extruded or tabletted silica pieces. Suitable powdered silicas typically have particles of surface weighted mean diameter D[3,2] in the range 3 to 100 $\mu$m and a BET surface area in the range 10 to 500 $m^2/g$. Granular silicas may have a variety of shapes and particle sizes, depending upon the mould or die used in their manufacture. For example the particles may have a cross-sectional shape which is circular, lobed or other shape and a length from about 1 to >10 mm. The surface area is generally in the range 10–500 $m^2/g$, preferably 100–400 $m^2g^{-1}$. The pore volume is generally between about 0.1 and 4 ml/g, preferably 0.2–2 ml/g and the mean pore diameter is preferably in the range from <2 to about 30 nm.

The cobalt compound is most preferably a cobalt ammine complex which is formed in situ in aqueous solution by dissolving basic cobalt carbonate in a solution of ammonium carbonate in aqueous ammonium hydroxide, to give a product of the desired cobalt content. The cobalt ammine carbonate solution may be made by dissolving basic cobalt carbonate in an aqueous solution of ammonium carbonate containing additional ammonium hydroxide. The relative amounts should be such that the pH of the solution is in the range 7.5 to 12, preferably 9 to 12. The solution preferably contains 0.1 to 2.5 moles of the cobalt complex per liter. As the concentration of cobalt increases, then generally the proportion of carbonate ions relative to hydroxide ions in the basic cobalt carbonate feed should be increased. The cobalt ammine complex compound is then heated, e.g. to a temperature in the range 60 to 110° C., to cause the cobalt ammine complex to decompose with the evolution of ammonia and carbon dioxide and to deposit a basic cobalt carbonate on the surface, and in the pores, of the silica. This step is conveniently carried out when slurrying silica powders with the cobalt compound so that the slurry is then maintained at the elevated temperature for a period, hereinafter the ageing period.

The amount of cobalt in the catalyst may be varied by varying the relative amount of cobalt and support present in the reaction mixture and by controlling the concentration of the solution of cobalt compound.

During the ageing step at least part of the silica dissolves and reacts with the cobalt complex to form a high surface area "cobalt silicate". Although cobalt silicates of various compositions may be formed, generally about one cobalt atom reacts to form "cobalt silicate" for each molecule of silica dissolved. The solid material comprising basic cobalt carbonate, "cobalt silicate" and any unreacted silica is then filtered from the aqueous medium, washed and dried.

Alternatively the cobalt compound is absorbed into the pore structure of the silica particle by impregnating the particle with the solution of cobalt compound. The impregnation may be repeated to increase the amount of cobalt compound absorbed by the silica particle, preferably with drying between each impregnation. The particles may then conveniently be separated from the remaining solution and the ageing process may be carried out by heating them e.g. to a temperature above 100° C. for the ageing period of at least 60 minutes, preferably at least 100 minutes to decompose the cobalt compound held within the particles to deposit basic cobalt carbonate in the structure of the silica particle. The particle may be subjected to successive impregnations, e.g. by separating them from the impregnation solution and drying before a subsequent impregnation.

The solid material may then be calcined in air, e.g. at a temperature in the range 250 to 450° C., to decompose the basic cobalt carbonate to cobalt oxide. The resultant catalyst precursor may be then reduced, e.g. with hydrogen, at a temperature between 300–550° C., more preferably below about 500° C., e.g. 380–500° C. Upon reduction, most, if not all, of the cobalt oxide is reduced to metallic cobalt but little or none of the "cobalt silicate" is reduced; the result is cobalt metal in a highly dispersed form, i.e. having a high cobalt surface area. Alternatively the basic cobalt carbonate may be directly reduced, i.e. without the need for a calcination step.

Preferably the amounts of silica and cobalt ammine carbonate employed are such that the cobalt to silicon atomic ratio is in the range 0.03 to 5. Irrespective of the cobalt content of the catalyst, the particle size of the catalyst is essentially the same as the particle size of the silica.

The catalysts of the invention preferably contain 3 to 75% by weight of total cobalt, more preferably below 60% by weight total cobalt. The amount of cobalt which is desirable varies according to the type of reaction for which the catalyst is used. Selection of an appropriate amount of cobalt is easily determined or known by the skilled person. Preferred catalysts typically have a cobalt surface area in the range 25 to >100 m$^2$ per gram total cobalt.

The cobalt surface area is determined by $H_2$ chemisorption. The sample (about 0.5 g) is degassed and dried under vacuum at 120° C. and then reduced by heating to 425° C. at a rate of 3° C. per minute whilst hydrogen gas is passed through the sample at a flow rate of 250 ml/min for 18 hours. The sample is then heated under vacuum to 450° C. over 10 minutes and maintained under those conditions for 2 hours. Following this pre-treatment, the chemisorption analysis is carried out at 150° C. using pure $H_2$ gas. The full isotherm is measured up to 800 mm Hg pressure of $H_2$ and the straight line portion of the chemisorption isotherm between 300 and 800 mm Hg is extrapolated to zero pressure to calculate the volume of the gas (V) which is chemisorbed by the sample. The metal surface area is then calculated from the following equation:

$$\text{Co surface area} = (6.023 \times 10^{23} \times V \times SF \times A)/22414 \quad \text{where}$$

$V$ = uptake of $H_2$ in ml/g $SF$ = Stoichiometry factor (assumed 2 for $H_2$ chemisorption on Co)

$A$ = area occupied by one atom of cobalt (assumed 0.0662 nm$^2$)

This method of calculating cobalt surface area is described in the Operators Manual for the Micromeritics ASAP 2000 Chemi System V 1.00, Appendix C, (Part no 200-42808-01, Jan. 18, 1991).

For hydrogenation reactions, the active form of the cobalt is elemental cobalt although in the active catalyst only some, rather than all, of the cobalt is normally reduced to the elemental form. Hence a useful measure is the exposed surface area of elemental cobalt per g of total cobalt present. Except where expressly indicated, as used herein, total cobalt contents are expressed as parts by weight of cobalt (calculated as cobalt metal, whether the cobalt is actually present as the metal or is in a combined form, e.g. as cobalt oxides) per 100 parts by weight of the catalyst or precursor thereto.

Useful catalyst products are formed by the dried precipitated product, a calcined (oxidic) product or a reduced product, depending on the use for which the catalyst is made. When a catalyst composition requires a step such as calcination and/or reduction to produce the active form of catalyst for the desired reaction, it may be referred to as a catalyst precursor.

In a non-reduced form the catalysts may be useful in oxidation reactions e.g. to oxidise organic compounds, for example as in the treatment of effluent containing organic material.

The catalysts, in reduced form, may be used for hydrogenation reactions such as the hydrogenation of aromatic or olefinic compounds, e.g. waxes, nitro, nitrile or carbonyl compounds, e.g. the conversion of nitrobenzene to aniline or the conversion of nitriles to amines or the hydrogenation of aldehydes to the corresponding alcohols. They may also be used for the hydrogenation of paraffin waxes to remove traces of unsaturation therein. They may also be useful in a wide range of other reactions, for example the Fischer-Tropsch process, i.e. where hydrogen and carbon monoxide are reacted in the presence of the catalyst to form higher hydrocarbons. This may be part of an overall process for the conversion of natural gas to petroleum compounds wherein the hydrogen/carbon monoxide gas mixture is a synthesis gas formed by steam reforming natural gas. The catalysts are particularly suitable for use in hydrogenation reactions, e.g. the hydrogenation of fatty nitrites and aldehydes.

The samples were tested using a CT5 crush strength testing instrument after drying at 100° C. The Co surface area was measured as described above, with the reduction of the catalyst taking place at 425° C. as a part of the experimental procedure, where indicated. The % Co was determined by inductively coupled plasma spectroscopy (ICPS). The results are shown in Table 1.

TABLE 1

| Number of Impregnations | Co surface area $m^2g^{-1}$ catalyst | Co surface area $m^2g^{-1}$ cobalt | Co content (% w/w reduced catalyst) | Co content (% w/w oxidic catalyst) | Crush strength $Nmm^{-1}$ |
|---|---|---|---|---|---|
| 0 | 0 | 0 | 0 | 0 | 5.7 |
| 1 | 5.0 | 32.6 | 15.3 | 14.7 | 9.4 |
| 2 | 7.7 | 38.6 | 20.0 | 18.8 | 8.6 |
| 3 | 6.9 | 26.1 | 26.4 | 24.9 | 6.6 |
| 4 | 7.2 | 23.2 | 31.1 | 29.2 | 4.6 |
| 5 | 6.0 | 17.1 | 35.1 | 32.8 | 4.5 |

The catalyst may be provided in the form of a concentrate of the catalyst particles dispersed in a suitable carrier medium, e.g. hardened soybean oil. Preferably the amount of catalyst in said concentrate is such that the concentrate has a total cobalt content of 5 to 30%, preferably 10 to 25% by weight.

When the catalyst is to be used in a reduced form, it may be supplied in non-reduced form, i.e. as a catalyst precursor, to be reduced in-situ before use or alternatively the catalyst may be reduced and then passivated in order to protect the reduced metal during subsequent storage and transport. Methods of protecting the catalyst are well known.

The invention is illustrated by the following examples in which, unless otherwise specified, all percentages and parts per million (ppm) are by weight.

EXAMPLE 1

A sample of a commercial extruded silica support available from Grace, was used having an approximately 1 mm circular cross-section, length between approximately 2–10 mm a BET surface area of about 255 $m^2$/g, a pore volume of about 1.14 ml/g and average pore diameter of about 18.1 nm.

A 5 liter aqueous stock solution was made up with 3760 g ammonia solution (SG 0.89, 30% ammonia), 1268 g ammonium carbonate and 1056 g cobalt carbonate. About 200 g of the silica support particles were placed into a beaker and covered with stock solution at ambient temperature for 2 minutes. The particles were then filtered and dried at 150° C. for 30 minutes. A sample was removed for testing and the remainder was reimpregnated. The procedure was repeated until five impregnations had been carried out. Each sample which was removed was treated in a rotary calciner at 280° C. for 2 hours.

EXAMPLE 2

Example 1 was repeated using a sample of a different commercial extruded silica support designated CS-1020E, available from PQ Corporation, was used having an approximately 2 mm circular cross-section and a length between 5–10 mm. The BET surface area was about 171 $m^2$/g, the pore volume of about 1.06 ml/g and average pore diameter about 24.9 nm. The shown in Table 2.

TABLE 2

| Number of Impregnations | Co surface area $m^2g^{-1}$ catalyst | Co surface area $m^2g^{-1}$ cobalt | Co content (% w/w reduced catalyst) | Co content (% w/w oxidic catalyst) | Crush strength $Nmm^{-1}$ |
|---|---|---|---|---|---|
| 0 | 0 | 0 | 0 | 0 | 7.1 |
| 1 | 4.5 | 37.2 | 12.1 | 11.7 | 11.0 |
| 2 | 7.5 | 42.6 | 17.6 | 16.8 | 11.1 |
| 3* | 10.1 | 46.2 | 21.9 | 20.8 | 11.0 |
| 4 | 8.9 | 36.9 | 24.1 | 23.3 | 11.6 |
| 5 | 13.7 | 48.6 | 28.2 | 26.3 | 10.3 |

*used in Example 5 reaction

EXAMPLE 3

Example 1 was repeated using a powdered silica support designated SP2-8290.04, available from Grace. The surface weighted mean diameter of the particles, D[3,2] was measured at 66 μm (D50=130 μm). The BET surface area was about 349 $m^2$/g, the pore volume (desorption) about 1.21 ml/g and average pore diameter about 134 Angstroms. The results are shown in Table 3.

EXAMPLE 4

A 4 liter aqueous stock solution was made up with 1918 g ammonia solution (SG 0.89, 30% ammonia), 198 g ammonium carbonate, 218 g basic cobalt carbonate and 1877 g demineralised water.

400 g of the SP2-8290.04 powdered silica support (described above) and sufficient of the stock solution to provide a Co:silica ratio of 5 wt % were charged to a stirred vessel equipped with a condenser. The initial pH of the aqueous solution was about 11.5. The mixture was heated to boiling while stirring and gentle boiling at about 100° C. was maintained for 3 hours, during which the solution became clear. The solid was filtered off, washed, dried in air at 150° C. for 1 hour and then calcined at 400° C. for 2 hours. The resulting catalyst was characterised as before and the results are shown in Table 3.

TABLE 3

| | Co surface area $m^2g^{-1}$ catalyst | Co surface area $m^2g^{-1}$ cobalt | Co content (% w/w reduced catalyst) | Co content (% w/w oxidic catalyst) |
|---|---|---|---|---|
| Example 3 | 1.4 | 22.5 | 6.2 | 6.0 |
| Example 4 | 1.6 | 32.0 | 5.0 | 4.9 |

EXAMPLE 5

Use of Catalyst in Fischer Tropsch Reaction

The catalyst from Example 2, made by 3 impregnations (21.85% Co measured in reduced form), was tested in a laboratory-scale Fischer Tropsch reaction, shown schematically below.

$$xCO + 2xH_2 \rightarrow (-CH_2-)_x + xH_2O$$

2.0 g of catalyst +5.0 g Csi (diluent) were charged to a stainless steel reactor. The catalyst was reduced at atmospheric pressure and under a continuous $H_2$ flow of 400 cm$^3$/min at 120° C. for 1 hour and then at 530° C. for 1 h. After reduction the reaction temperature of 220° C. was established, and then the system was pressurised to 20 bar under $H_2$ flow. CO was slowly introduced in the system to provide a gas feed ratio of 2:1 ($H_2$:CO). The products were collected and analysed by gas chromatography. The average results over an 8 hour steady state period are shown below.

| | |
|---|---|
| Av CO conversion (%) | 6.7 |
| Prod. Distribution (% C): $CO_2$ | 3.3 |
| R—OH | .0 |
| Hydrocarbons | 96.7 |
| Hydrocarbon selectivity (wt %): $C_1$ | 25.1 |
| $C_2$—$C_4$ | 26.3 |
| $C_{5+}$ | 48.6 |
| Chain growth probability $\alpha(C_2$—$C_{32})$ | 0.75 |

What is claimed is:

1. A process for manufacturing a catalyst which comprises a cobalt species on a solid silica support, comprising mixing together particles of a solid silica support and an aqueous solution of cobalt ammine carbonate, and heating to an elevated temperature sufficient to effect decomposition of the cobalt ammine carbonate and precipitation of a basic cobalt carbonate onto said support.

2. A process as claimed in claim 1, comprising saturating silica support particles with an aqueous solution of cobalt ammine carbonate, and removing the excess of the solution, before heating the resulting product to a temperature sufficient to effect decomposition of the cobalt ammine carbonate.

3. A process as claimed in claim 1, wherein the mixture of solid support and said cobalt solution is heated to a temperature sufficient to effect decomposition of the cobalt ammine carbonate in situ before separating the solid catalyst from the mixture and drying.

4. A process as claimed in claim 1, wherein the solid support and cobalt solution are maintained at an elevated temperature for a period of at least 60 minutes.

5. A process as claimed in claim 1, wherein said temperature is in the range 60–110° C.

6. A process as claimed in claim 1, further comprising the step of calcining the resulting product at a temperature between 200 and 600° C.

7. A process as claimed in claim 1 further comprising the step of reducing the resulting product with hydrogen at a temperature between 300–550° C.

8. A process for the production of a catalyst comprising heating a slurry of particles of silica suspended in an aqueous solution of a cobalt ammine carbonate for a total period of at least 60 minutes at a pH above 7.5 at an elevated temperature sufficient to effect decomposition of the cobalt ammine carbonate and precipitation of a basic cobalt carbonate, and thereafter filtering the precipitated basic cobalt carbonate residue from the aqueous medium.

9. A catalyst or catalyst precursor made by the process claimed in claim 1 or claim 8.

10. A process for the hydrogenation of an organic compound comprising an olefinic, carbonyl, nitrile, nitro or aromatic group; comprising reacting said compound with hydrogen in the presence of a catalyst as claimed in claim 9.

11. A process for the hydrogenation of an organic compound comprising an olefinic, carbonyl, nitrile, nitro, or aromatic group, comprising forming an active catalyst in situ by reducing a catalyst precursor as claimed in claim 9 with hydrogen, and conducting said hydrogenation reaction by reacting said compound with hydrogen in the presence of said active catalyst.

12. A process for the formation of a hydrocarbon by the reaction of carbon monoxide with hydrogen in the presence of a catalyst as claimed in claim 9.

13. A process for the formation of a hydrocarbon by the reaction of carbon monoxide with hydrogen, comprising forming an active catalyst in situ by reducing a catalyst precursor as claimed in claim 9 with hydrogen before conducting said reaction, and forming a hydrocarbon by reacting carbon monoxide with hydrogen in the presence of said active catalyst.

14. A process for the oxidation of an organic compound by reaction with an oxygen-containing compound in the presence of a catalyst as claimed in claim 9.

* * * * *